(12) United States Patent
Fagan

(10) Patent No.: US 7,211,444 B2
(45) Date of Patent: May 1, 2007

(54) WAVEGUIDE AND ASSAY

(75) Inventor: John Fagan, Fairfield, IA (US)

(73) Assignee: Genetic ID NA, Inc., Fairfield, IA (US)

( * ) Notice: Subject to any disclaimer, the term of this patent is extended or adjusted under 35 U.S.C. 154(b) by 614 days.

(21) Appl. No.: 10/134,272

(22) Filed: Apr. 26, 2002

(65) Prior Publication Data

US 2002/0168677 A1    Nov. 14, 2002

Related U.S. Application Data

(60) Provisional application No. 60/287,038, filed on Apr. 27, 2001.

(51) Int. Cl.
  *G01N 33/552*    (2006.01)
(52) U.S. Cl. ............... 436/527; 385/12; 385/125; 385/141; 385/142; 385/143; 385/144; 385/145; 422/82.11; 435/6; 435/287.2; 435/288.7; 435/808; 436/164; 436/172; 436/524; 436/535; 436/805; 436/510
(58) Field of Classification Search ............... None
See application file for complete search history.

(56) References Cited

U.S. PATENT DOCUMENTS

| | | | | | |
|---|---|---|---|---|---|
| 3,814,497 | A | * | 6/1974 | Stone | 385/125 |
| 3,841,731 | A | * | 10/1974 | Midwinter | 385/125 |
| 3,894,788 | A | * | 7/1975 | Gambling et al. | 385/125 |
| 5,333,227 | A | * | 7/1994 | Ishiharada et al. | 385/100 |
| 5,546,493 | A | * | 8/1996 | Noguchi et al. | 385/125 |
| 5,570,447 | A | * | 10/1996 | Liu | 385/125 |
| 5,881,200 | A | | 3/1999 | Burt | |
| 6,011,882 | A | * | 1/2000 | Dasgupta et al. | 385/12 |
| 6,020,207 | A | * | 2/2000 | Liu | 436/164 |
| 6,163,641 | A | * | 12/2000 | Eastgate | 385/125 |
| 6,813,427 | B1 | * | 11/2004 | Kaltenbacher et al. | 385/125 |

FOREIGN PATENT DOCUMENTS

| | | |
|---|---|---|
| WO | WO 9512138 A1 * | 5/1995 |
| WO | WO 9957584 A1 * | 11/1999 |
| WO | WO 00/10044 | 2/2000 |

OTHER PUBLICATIONS

Deacon, J.K. et al. (1991) Biosens Bioelectron. 6:193-199.
Golden, J.P. et al. (1994) IEEE Trans Biomed. Eng. 41:585-591.
Gunasingham, H. and Tan, C.H. (1992) Biosens. Bioelectron. 7:353-359.
Kusterbeck, A.W. et al. (1990) J. Immunol. Methods 135:191-197.
Misiakos, K. and Kakabakos, S.E. (1998) Biosens. Bioelectron. 13:825-830.
Piunno, P.A. et al. (1995) Anal. Chem. 67:2635-2643.
Plowman, T.E. et al. (1999) Anal. Chem. 71:4344-4352.
Pollard-Knight, D. et al. (1990) Ann. Biol. Clin. (Paris) 48:642-646.
Quinn, J.G. et al. (Jun. 2000) Anal. Biochem. 281:135-143.
Rabbany, S.Y. et al. (1994) Crit. Rev. Biomed. Eng. 22:307-346.
Schaffar, B.P. and Wolfbeis, O.S. (1990) Biosens. Bioelectron. 5:137-148.
Wemhoff, G.A. et al. (1992) J. Immunol. Methods 156:223-230.
Yeakley, J.M. et al. (Apr. 2002) Nat. Biotechnol. 20:353-358.

* cited by examiner

*Primary Examiner*—Christopher Chin
(74) *Attorney, Agent, or Firm*—GreenLee, Winner and Sullivan, P.C.

(57) ABSTRACT

A fluidic waveguide comprising a container and a fluid that fills said container, wherein said fluid has a refractive index greater than the refractive index of the wall of said container and wherein said fluid can act as a waveguide for electromagnetic radiation when contacted therewith is disclosed. A corresponding fluidic lightguide along with devices that function as composite waveguides and lightguides are described. Assays utilizing this waveguide for biochemical, chemical, and other kinds of analyzes are also disclosed.

52 Claims, No Drawings

WAVEGUIDE AND ASSAY

This application claims priority of U.S. Provisional Application Ser. No. 60/287,038, filed Apr. 27, 2001, the disclosure of which is hereby incorporated by reference in its entirety.

FIELD OF THE INVENTION

This invention relates to the field of waveguides and to assays that use such waveguides for biochemical, chemical, and other kinds of analyses.

BACKGROUND OF THE INVENTION

There are a wide variety of assays available in the art, including, but not limited to, those that assay for the presence or absence or amount of a polynucleotide, protein, organism, or other molecular species and the like.

Recent efforts have attempted to employ waveguide technology in performing such assays. The presence and/or absence and/or quantity of a material to be analyzed (the "analyte") is determined by use of fluorescent material that functions as a reporter with the fluorescent material being excited during the assay and the light emitted from the fluorescent material being directed to a detector by the use of a waveguide.

One such example is an optrode. (see refs. 1–3). The optrode is an optical fiber having probe molecules, typically antibodies, immobilized at its distal ends. Excitation light is delivered through the fiber to the probe-target-reporter complexes that form at the end of the fiber. The resultant fluorescent emission is wave-guided back up the fiber to an optical system that delivers the emitted light to a photomultiplier tube or other detector. The key role of the fiber in this sensor is that both excitation and emission light is guided through the fiber very efficiently due to the phenomenon of total internal reflection (TIR). Optical fibers are specially designed so that the index of refraction of the fiber ($n_f$) is greater than the index of refraction of the material cladding the fiber ($n_c$). When light, introduced into the fiber from any source, strikes the fiber-cladding interface, it will be reflected with essentially 100% efficiency, due to the phenomenon of TIR, as long as the angle of incidence is less than the critical angle ($\theta_c$), which is defined as $$\theta_c = \sin^{-1}(n_c/n_f).$$

Sensitivity of such sensors is greatly enhanced by the efficiency with which light is guided via TIR from the probe-derivatized surface of the sensor, through the fiber, to the detector.

Recently this basic approach has been expanded upon to develop manifolds in which several probes are applied as small spots on the distal surface of a single fiber optic. Optical systems were designed to assess interactions between probes and targets individually. A similar, but more powerful system has been devised in which micron-scale optical fibers are configured as a manifold in which indentations at the end of the manifold receive small beads of different colors, each of which is derivatized with a different oligonucleotide probe, and to which the corresponding target and reporter are bound (4). This system provides a reusable fiber-optical manifold that can be used to assess hybridization of any set of targets to their respective probes.

Optrodes have found applications in a number of areas, but have significant limitations in that the area is limited to which probe molecules can be coupled. This limits the sensitivity of the sensor. Another limitation is that fluorescence emitted from any molecule located in the vicinity of the sensing terminus of the fiber will be picked up by the fiber, which contributes significant levels of background noise.

Another sensor is an evanescent wave-based sensor (1,5, 6). When light strikes the interface between the optical fiber and the surrounding medium, which is of lower index of refraction, it undergoes total internal reflection. However, an electromagnetic component of the light passes through the interface, and is propagated through the surrounding medium in a direction parallel to the fiber. This is called the evanescent wave. It penetrates only a short distance (a fraction of the wavelength of the light used) into the medium surrounding the fiber, decaying exponentially as a function of the wavelength of the light. However, this wave can effectively excite fluorescent compounds located close to the fiber surface.

Although other designs have been devised (7), the most common design for evanescent wave-based sensors is to immobilize probe molecules on the walls (not the distal end) of the fiber. Probe-target-reporter complexes formed on the surface of the fiber are detected when the evanescent wave excites the reporter fluor molecules, which emit fluorescence, and which when it strikes the fiber wall at appropriate angles will enter the fiber and be wave-guided up the fiber to the detector.

This design has the advantage over the optrode that fluor molecules in the bulk solution surrounding the fiber are not excited because the evanescent wave does not propagate significantly into the bulk solution phase. Only free fluors that happen to be located within about 0.5 wavelength of the fiber wall will be excited. This reduces background fluorescence that is picked up by the bulk solution surrounding the fiber.

The disadvantage of this approach is that the power of the evanescent wave is at most 2% of the power of the excitation light within the fiber. Thus, effective excitation of the probe-target-reporter complexes can be challenging. Similarly, a large proportion of the fluorescence emitted by probe-target-reporter complexes fails to be coupled into the fiber, because of the unfavorable geometry of the system. Both of these features limit the sensitivity and utility of evanescent wave sensors.

Another sensor involves the use of non-evanescent-wave-based fiber optic systems (8). The limitation with evanescent wave-based sensors is the inefficiency with which excitation light can be transmitted out of the fiber to the probe-target-reporter layer, and the inefficiency with which fluorescence is coupled back into the fiber to be waveguided to the detector. Other mechanisms have been used in attempts to increase these efficiencies. For instance, attempts have been made to match the index of refraction of the probe layer with that of the fiber. The intention in this design is to include the probe layer within the waveguide so that a larger portion of the exciting light reaches probe-target-reporter complexes, and a larger portion of emitted fluorescence is coupled into the waveguide. Empirical evidence indicates that fibers constructed based on this principle function with somewhat improved efficiency compared to evanescent wave-based sensors.

A further example is a surface plasmon resonance-based sensor (1,9,10). Sensors based on the surface plasmon resonance phenomenon have the advantage that they directly detect changes in index of refraction at the surface of the optical system due to binding of target to probe. Thus, this method does not require the use of fluorescent or other reporter molecules.

This optical system consists in simplest form of a prism, one surface of which is coated with a thin metal film (usually gold or silver). Probe molecules are attached to the other surface of the metal film, which is also in contact with a solution that may contain the analyte or target of interest.

The evanescent wave generated by light impinging on the prism-metal interface at a certain incident angle, termed the resonant angle or SPR angle, will couple with and excite the free-electron plasma of the metal film. That is, electromagnetic coupling occurs between the free electrons of the metal film and the evanescent wave of the light that undergoes total internal reflection at the SPR angle within the prism. This generates a resonant wave that propagates along the surface of the metal. Dissipative processes within the metal film absorb some of the energy of this resonant wave. As a result, the light incident upon the prism-metal interface at the SPR angle is reflected with attenuated intensity. In other words, at the SPR angle, light energy is transformed into dissipative surface plasmons within the metal. This is observed as attenuation of the total internal reflection in the prism.

The SPR angle depends not only on the properties of the metal film but also on the dielectric constant (and thus the index of refraction) of the medium immediately adjacent (within a fraction of one wavelength) to the other surface of the metal film. This is because of interaction between the evanescent field of the SPR wave and the medium immediately adjacent to the metal film. Materials that bind to the surface of the metal film alter the dielectric constant (and index of refraction) in that zone, altering the SPR angle. This is observed as a change in the angle at which total internal reflection is attenuated.

This change in the SPR angle is a sensitive indicator of binding to the metal surface, and can act as a sensor for specific molecular species (target molecules) present in a solution that bathes the metal surface. To accomplish this, probe molecules are bound to the metal film. When target molecules are present in the solution bathing the metal film, they form complexes with the immobilized probe. This changes the index of refraction immediately adjacent to the metal surface, which, in turn, alters the SPR angle. The change in SPR angle can be directly measured. With proper calibration, such a system can be used to directly and quantitatively measure the formation of probe-target complexes.

BRIEF SUMMARY OF THE INVENTION

In one aspect, the present invention relates to a fluidic waveguide comprising a container and a fluid that fills said container, wherein said fluid has a refractive index greater than the refractive index of the wall of said container and wherein said fluid acts as a waveguide when contacted with electromagnetic radiation.

In another aspect, the present invention relates to a fluidic waveguide comprising a container and a fluid that fills said container, wherein the interior surface of said container is covered by an optical coating element and said fluid has a refractive index higher than the refractive index of said coating element and wherein said fluid acts as a waveguide when contacted with electromagnetic radiation.

In preferred embodiments of this invention, said optical coating has a width or thickness of at least 100 Angstroms, preferably a width or thickness of at least 100 Angstroms but not more than one micrometer, most preferably a width or thickness of at least 500 Angstroms but not more than one micrometer, especially a width or thickness of at least 0.1 micrometer but not more than one micrometer, most especially a width or thickness of at least one micrometer In a further aspect, the present invention relates to a fluidic waveguide, comprising a container and a fluid that fills said container, wherein said fluid has a refractive index less than or equal to the refractive index of the wall of said container, wherein the outer surface of said container is covered by an external medium wherein the wall of said container has a refractive index greater than the refractive index of said medium and whereby said fluid and said container function together as a composite waveguide when contacted with excitatory electromagnetic radiation.

In a still further aspect, the present invention relates to a fluidic lightguide comprising a container and a fluid that fills said container, and an internally reflective coating element covering the outer surface of said container wherein said container functions as a lightguide when contacted with electromagnetic radiation.

In preferred embodiments, the fluidic waveguides and/or lightguides of the invention, whether composite or otherwise, may comprise a probe. In further embodiments thereof, said probe is attached to the inner surface of the wall of the container or is in solution in the liquid filling said container or may be attached to solids present in the cavity of the container.

In other preferred embodiments, the probe may be one or more of an oligonucleotide, an antibody, an aptamer, a catalyst and an enzyme.

In further preferred embodiments, the waveguides and/or lightguides of the invention may comprise a reporter molecule, especially where said reporter molecule is a member selected from the group consisting of a fluorophore and reagents capable of producing a fluorophore.

Still further preferred embodiments of the waveguides and/or lightguides of the present invention includes cases where these comprise a probe and one or more reporter molecules that generate a signal when said probe is contacted with an analyte, especially where the probe is attached to the inner surface of the wall of said container. In one such preferred embodiment, the reporter molecule is a quantum dot.

The present invention also relates to a manifold of integrated non-identical fluidic lightguides and/or lightguides, including manifolds of both waveguides and lightguides, as disclosed herein. In a preferred embodiment, said manifold is portable.

In additional preferred embodiments of the waveguides, lightguides and manifolds of the invention, the fluid in the container is a liquid, or possibly a gel.

The present invention also relates to a method of determining an analyte in a sample comprising contacting said analyte with a waveguide or lightguide of the invention, including manifolds of these, contacting said waveguide or lightguide with electromagnetic radiation and detecting a signal wherein said signal indicates the presence of said analyte in said sample, thereby determining said analyte in said sample.

When said waveguide comprises an optical coating, said optical coating is thicker than one wavelength, preferably more than two wavelengths, of said electromagnetic radiation.

In preferred embodiments of the methods of the invention, the source of electromagnetic radiation is a laser or a white light source.

In additional preferred embodiments, the intensity of said signal is proportional to the amount of said analyte in said sample and/or wherein said detection of a signal comprises detecting electromagnetic radiation. In one preferred embodiment, the signal is produced by a fluorescent molecule.

In another preferred embodiment of the methods of the invention, the analyte comprises a reporter molecule that generates a signal when the probe is contacted with the analyte.

DETAILED DESCRIPTION OF THE INVENTION

In one aspect, the present invention relates to fluidic waveguide that results from introduction of a fluid, preferably a liquid, but also possibly a gel, into a container that is in the form of a channel, tube, or other hollow structure, wherein the refractive index of said fluid is greater than the refractive index of the wall of the container. Said fluid, preferably a liquid, in the container functions as a waveguide in the sense that light directed into the fluid at angles less than the critical angle for the system undergoes total internal reflection at the interface between the fluid and container.

In another aspect, the present invention relates to a fluidic waveguide, as defined above, for delivering emitted fluorescent light from a fluorophore to a light detector that is comprised of a container that is in the form of a channel, tube, or other hollow structure that contains a fluid, preferably a liquid, but could also be a gel, with the container further including a fluorophore (in the liquid and/or on a wall of the container) wherein the refractive index of the fluid, preferably a liquid, is greater than the refractive index of the wall of the container. The fluid, preferably a liquid, in the container functions as a waveguide to direct light emitted from the fluorophore to a light detector.

Thus, the present invention relates to a fluidic waveguide comprising a container and a fluid that fills said container, wherein said fluid has a refractive index greater than the refractive index of the wall of said container and wherein said fluid acts as a waveguide when contacted with electromagnetic radiation.

The container for the fluid, preferably a liquid, is advantageously a channel, tube, or other hollow structure, ranging in diameter from a few microns to a few millimeters, and preferably from a millimeter to a few centimeters in length, but could be of either larger or smaller dimensions and the term "container" is understood herein to encompass all such structures.

The fluid, preferably a liquid, in the lumen of the container may include dissolved solids and may be comprised of one, two or more fluids. Thus, the term "fluid" encompasses "gas," "gel," "liquid," and the latter encompasses a "solution." The fluid could also include a suspension.

The lumen or open portion of the container may include a solid in addition to a fluid. In such a case, the refractive index of the liquid and the solid should be essentially equal to each other.

In a preferred embodiment, the interior or lumen of the container is essentially filled with fluid, or a combination of liquid and solid, in which case the liquid and solid have essentially equal refractive indexes.

In accordance with another aspect of the present invention, there is provided a fluidic wave guide for use in an assay for an analyte that uses a fluorescent material as the reporter material for the assay, wherein the container in which all or a portion of the assay is performed, and/or fluid in the container, functions as a waveguide to transmit emitted light from the fluorescent reporter to a light detector, with such emitted light being used as a read-out of the assay for determining analyte.

The container for the fluid can be in the form of a tube, as described above.

The assay reagents include an analyte, a probe, or a probe system, and a reporter in the form of fluorescent material or material that becomes fluorescent through physical, chemical or biochemical processes.

The probe, or probe system, includes a material that interacts with analyte (binds to or reacts with the analyte, or catalyzes the chemical transformation of the analyte) and may further include one or more materials that interact with a material that interacts with the material that detects, or interacts with, the analyte or with a material produced by interaction with a material produced by the interaction between the analyte and the material that interacts with the analyte.

The reporter may be originally present in the assay reagents or may be produced and become part of the assay reagents during the assay. Alternatively, the reporter may be chemically linked to the probe or probe system.

In one embodiment, the lumen or opening in the container, which may be in the form of a capillary tube, includes a solid in addition to the fluid, with such solid functioning as a support for all or a portion of the probe, or probe system. The solid is preferably porous or gel-like so that the opening in the tube can include liquid as well as the solid. As hereinabove indicated, the refractive index of the solid in the lumen and the fluid, preferably a liquid, in the lumen should be essentially equal to each other whereby the solid and fluid, preferably a liquid, in the lumen function as a composite waveguide.

In a preferred embodiment, all or a portion of the probe, or probe system, may be attached to the wall of the container. This coating of probe on the wall of the container may also include a reporter molecule or group or reporter moiety. Fluorescent material and the reporter may be attached or linked to a probe material attached to the container wall. Alternatively, the reporter may reside in the fluid present in the lumen of the container.

Thus, the present invention relates to a fluidic waveguide comprising a container and a fluid that fills said container, wherein the interior surface of said container is covered by a optical coating element and said fluid has a refractive index higher than the refractive index of said coating element and wherein said fluid acts as a waveguide when contacted with electromagnetic radiation. As used herein, the term "optical coating element" refers to a coating that acts to alter the optical properties of the system, such as a refractive coating.

In preferred embodiments of this invention, said coating has a width of at least 100 Angstroms, preferably a width of at least 100 Angstroms but not more than one micrometer, most preferably a width of at least 500 Angstroms but not more than one micrometer, especially a width of at least 0.1 micrometer but not more than one micrometer, most especially a width of at least one micrometer A device in accordance with the invention includes:
1. A container, which is preferably a tube, channel, or other hollow structure, all encompassed in the term "tube," or "tubular sensor element."
   a. The tubular sensor element is to be distinguished from other tubular or channel-like elements that may be used in a fluidics system of the analytical device as a whole, in that the tubular sensor element is the site where the core analytical events of the over-all analytical process take place. In particular, the tubular sensor element is not merely a fluidic element but functions as an optical unit and can also function as a chemical unit in that it acts as a waveguide and may include a probe or probe molecules to interact with an analyte passing through the container.
   b. The tube can be made of glass or related materials, plastics, semiconductor materials, and the like.
   c. The tube can be cylindrical or conical or of other geometry selected to achieve optimal optical and fluidic function.
   d. The composition, shape, chemistry, and optical, as well as other characteristics of the tube are dictated by the following:
      i. The optical design of the system.
      ii. The fluidic design of the system.
      iii. The chemistry of the analytical process and of the analyte or target molecule.
      iv. The chemistry of the probe molecule and reporter system.
      v. Other relevant characteristics of the analytical system.
2. A fluidics or microfluidics system.
   a. The fluidics system can be integrated into, or it can be attached to, the tubular sensor element of the device.
   b. The fluidics system can function to accomplish the delivery, removal, and movement of fluids to and through the detector tube.
   c. This system can also function to fractionate, process, or otherwise modify the analytical sample before it is delivered to the tubular sensor element, and can include a range of functional elements including but not limited to electrophoretic elements, filtering elements, size-sorting elements, pumps, and others.
   d. Fluidics functions can be accomplished by very simple manual procedures that make use of capillary action or other simple processes, or by complex fluidic, electrical, electronic, or mechanical systems.
3. A fluid, preferably a liquid, that fills the lumen of the tubular sensor element, whose physical, chemical, and optical characteristics depend on the following:
   a. The optical design of the system,
   b. The fluidic design of the system,
   c. The physics and chemistry of the analyte,
   d. The physics and chemistry of the detection system (probe and reporter).
4. Probe molecules.
   a. The physical, chemical, and biological properties of the probe molecules, and their location within the analytical system will be dependent on the following:
      i. The optical design of the system.
      ii. The fluidic design of the system.
      iii. The chemistry of the analytical process, the reporter system, and the analyte or target molecule.
      iv. Other relevant characteristics of the analytical system.
   b. Probes maybe
      i. Attached to or coated on the inner wall of the tubular sensor element,
      ii. Present in solution in the liquid contained in the lumen of the tube,
      iii. Attached to solid material located in the lumen of the tubular sensor element.
   c. If the probe molecules are coated onto, or immobilized to the inner walls of the tube or to a solid material located in the lumen of the tube, then this is accomplished by processes that preserve the chemical and physical activity and specificity of the probe molecules towards the analytes or targets of interest.
   d. The molecular recognition process between probe and analyte may take the following non-limiting forms:
      i. In some cases, this process is a simple binding reaction, in which an intermolecular complex is formed between analyte and probe. The formation of this complex immobilizes the analyte to the inner wall or to the solid material in the lumen of the tubular sensor element. The immobilized probe-analyte complex is then detected by a reporter system that may function via a variety of mechanisms, such as the binding of dyes specific for the structure of that complex, or the binding of fluorescently labeled antibodies, nucleic acid molecules, or other molecules that recognize either the analyte or the analyte-probe complex.
      ii. In some cases, the probe-target recognition system is designed such that binding of the probe to the analyte may catalyze or otherwise bring about molecular transformations of the analyte, generating fluorescent products either directly or via linked reactions.
   e. Non-exhaustive examples of probe molecules are as follows:
      i. Single stranded oligomers or polymers of nucleic acid or nucleic acid analogues, which can specifically interact with and bind to analyte nucleic acid molecules based on sequence homology between the probe and analyte nucleic acid molecules. This interaction occurs primarily via hydrogen bond-based interactions between the nucleotides of the two nucleic acid strands;
      ii. Antibodies and aptamers, which can specifically interact with and bind to a wide variety of molecules and molecular complexes. Potential targets include, but are not limited to, the following: small organic molecules, biologically important polymers such as proteins, nucleic acids, and carbohydrates, other man made polymers/molecules, and complex biological structures such as membrane-protein complexes, receptor-target complexes, antibody-antigen complexes, cell surface markers, cells of any organism, and the like.;
      iii. Enzymes, which can interact with, and catalyze the chemical transformation of, a diverse range of molecular species;
      iv. Other biological molecules, molecular complexes, and larger biological entities, and organic or inorganic molecular species, either natural or synthetic, that can (a) bind to, (b) chemically react with, or (c) catalyze the transformation of analytes carried in the tubular sensor element.
5. Optical system
   a. The optical system will be designed to efficiently deliver excitation light to the reporter molecules for analytical and/or chemical purposes and to collect fluorescence emitted light from the reporter.
   b. The characteristics of the optical system will be dependent on the following:
      i. The physics and chemistry of the analytical process, the reporter system (fluorescent dyes), and the analyte or target molecule,
      ii. The physical and optical characteristics of the tubular sensor element and the fluid (and porous solid) contained in the lumen of the tube,
      iii. The fluidic design of the system,
      iv. Other relevant characteristics of the system.

c. Light will be delivered to the probe surface via a fluidic waveguide whose functional elements can include the following:
   i. The fluid, preferably a liquid, phase alone or in combination with a porous solid phase that matches the refractive index of the liquid contained in the lumen of the tube,
   ii. A probe coating on the inner wall of the tubular sensor element,
   iii. Optical coatings on the inner wall of the tube,
   iv. The tube wall, itself,
   v. Optical coatings and cladding applied to the outer surface of the tubular sensor element.
d. The indexes of refraction of the following elements will be adjusted to achieve the desired optical characteristics of the system for the particular application of interest:
   i. The tubular sensor element,
   ii. The material (fluid, preferably a liquid, and solid) in the lumen of the tube.
   iii. The optical coatings and treatments of the inner surface of the tube. (including that of the probe molecule layer, if applicable).
   iv. The optical coatings and treatments of the outer surface of the tube, if such surface exists.
e. In addition to the fluidic waveguide, the primary elements of the optical system will include but are not restricted to the following:
   i. Light source or sources,
   ii. Detector for emitted fluorescence,
   iii. Lenses, filters, gratings, monochrometers, beam splitters, coatings, and other devices to control, modify, and modulate the excitation and emission light,
   iv. All components will be optimized to achieve the maximum sensitivity, consistency, and quality of the optical signal.
6. Coatings—The device may include a variety of coatings, treatments, modifications of the inner and outer surfaces of the tube or other elements, such as porous solids contained in the lumen of the tube, to confer desired optical, chemical, and physical properties to the system.
   a. Coatings can be deposited by any process, whether chemical, physical, or other.
   b. Coatings can be deposited in any order appropriate to achieve the desired optical, chemical and physical properties.
   c. The order of placement of the probe surface with respect to other coatings can vary.
   d. The coating on the inner wall of the tube, which may include probe and other assay reagents, may function in conjunction with the liquid in the lumen of the tube as a composite waveguide. Alternatively the thickness of the coating may be controlled such that it is less than one wavelength of the emitted light, whereby essentially only the fluid, preferably a liquid, functions as a wave guide for the emitted light.

In a preferred embodiment, the fluid, preferably a liquid, phase in the lumen of the tube, which includes a portion of the assay reagents (for example, the analyte), has an index of refraction ($n_l$) that is greater than the index of refraction of the inner wall of the tube ($n_w$). The index of refraction of the coating on the inner wall of the tube that is exposed to the fluid, preferably a liquid, phase in the lumen has an index of refraction ($n_c$) that is equal to or greater than or in some cases less than the index of refraction of the fluid, preferably a liquid, phase.

In this embodiment, the fluid, preferably a liquid, phase alone functions as a waveguide, or the fluid, preferably a liquid, phase and the assay reagent coating applied to the inner wall of the tube constitute a composite waveguide. The desired configuration of indexes of refraction is achieved by selecting materials for the tube, or inner coatings of the tube, that are of low n, and for the fluid, preferably a liquid, that are of high n. For instance there are urethane polymers that have n as low as 1.35, while even common solutes such as sucrose increase the n of aqueous solutions well above 1.35. It should be noted that coatings used to lower the n of the tube must be greater in thickness than 1 wavelength of the emission light and preferably 2 or more wavelengths thick. Solutes used to fortify the lumenal fluid, preferably a liquid, are selected on the basis of two primary criteria: (1) they have a high index of refraction, and (2) they do not inhibit or interfere with, but may even enhance, the chemistry involved in the probe-analyte-reporter recognition process. High n can be achieved in the probe coating by adjusting the attachment chemistry to achieve probe densities that are sufficient to increase $n_c$ of the layer above that of the tube. Other strategies can also be used. TIR occurs at the interface between the probe coating and the tube wall or at the interface between the fluid, preferably a liquid, and the coating, depending on the indexes of refraction of these elements and depending upon the thickness of the coatings.

Electromagnetic radiation, such as excitatory light, for example, from a laser or a white light source, is delivered through the waveguide to probe-analyte-reporter complexes optionally part of the waveguide. Fluorescence emitted at angles below the critical angle for TIR for the interface between an assay reagent coating and the container wall or fluid, preferably a liquid, will be waveguided through the lumen-probe-coating composite or the fluid, preferably a liquid, to a detector. Light emitted in the direction of the detector will be delivered directly to the detector, while light emitted toward the opposite end of the tube will propagate to that end of the tube, where it will encounter a reflective surface that will reflect it toward the detector.

Fluorescence emitted at angles greater than the critical angle for TIR will pass through the inner wall of the tube, and will be lost through the wall. Alternatively, a coating of reflective material can be applied to reflect this light back into the tube wall, where it can propagate directly or indirectly towards the detector. This light will be recovered with lower efficiency, due to the inefficiency of such reflective surfaces, but contributes to increasing the overall efficiency of light/signal recovery.

In another preferred embodiment, the inner wall of the tube is coated with a highly reflective material that allows efficient reflection of both the excitation and emission wavelengths. The container wall serves as a support in this design, but does not serve a functional role in the optics of this system. In this embodiment, the index of refraction of the fluid, preferably a liquid, in the lumen of the container, such as a tube, is not critical to the functioning of the analytical system, nor is that of the probe coating, as long as that coating is thin in comparison with the wavelength of the excitation light used in the analytical system. Under these conditions, the fluid, preferably a liquid, in the lumen of the tube and the probe coating function as a composite light guide.

In this embodiment electromagnetic radiation, such as excitatory light, for example, from a laser or a white light source, is delivered through this composite light guide to probe-analyte complexes that are suspended in and are actually an integral part of the lightguide. Fluorescence emitted at all angles will be reflected toward one end of the container or the other. That which is emitted in the direction of a detector will be guided directly to the detector, while light emitted toward the opposite end of the container propagates to that end of the container, where it will encounter a reflective surface that will deflect it toward the detector.

Unlike the other embodiments, the reflective process used in this configuration to guide light to a detector is less efficient than the total internal reflection (TIR) process. TIR occurs only when light impinges upon an interface between two materials of different indexes of refraction, traveling from the material of greater index of refraction to the material of lower index of refraction, where the light is reflected back into the material of higher refractive index. Because the light guide in this particular embodiment does not function by TIR, light intensity will be progressively reduced as it propagates via multiple reflections along the light guide, with some emissions being completely dampened and thus extinguished. The degree of reduction depend on several factors, including the angle at which the light strikes the tube wall (the higher the angle the more reflections will be required for the light to traverse the length of the tube and strike the detector, and the greater the loss of signal intensity), the characteristics of the reflective coating (because different coatings confer different efficiencies of reflection), and the wavelength of light (because efficiency of reflection for different surfaces varies for different wavelengths of incident light).

In another preferred embodiment the n of the lumenal fluid, preferably a liquid, is less than or equal to the n of coatings on the inner wall (including the coating of probe molecules), the n of the tube wall, and the n of the tube wall will be greater than n of the surrounding medium. In this case, the tube, inner coatings, and lumenal fluid will all function as a single composite optical waveguide. Electromagnetic radiation, such as excitatory light, will be delivered to the probe-analyte-reporter complexes attached to the inner surface of the tube both via the fluid contained in the lumen of the tube and via the walls of the tube.

Fluorescence emitted by the immobilized probe-analyte-reporter complexes will be collected across the whole cross-section of the composite waveguide, which includes the fluid within the lumen and the wall of the tube, as well as any coatings on the walls of the tube that are capable of transmitting light. Only very low angles will be delivered directly, without reflection or refraction through the lumen to the detector. The remainder of the light will impinge upon the wall of the tube, will enter the wall and will be refracted and strike the outer wall. Some of that light, that which impinges on the outer surface of the wall at angles less than or equal to the critical angle for TIR from the outer wall surface, will undergo TIR and will be guided by the composite wave guide either to the detector, or to the opposite end of the wave guide where it will be reflected back toward the detector.

Light that strikes the outer surface of the wall at angles greater than the critical angle for TIR will be lost through the wall of the tube. Alternatively, a coating of reflective material can be applied to the outer wall of the tube to reflect light having incident angles greater than the angle of TIR back into the composite waveguide, where it can propagate directly or indirectly to the detector. This light will be recovered with lower efficiency, due to the inefficiency of such reflective surfaces, but will contribute to increasing the overall efficiency of light/signal recovery.

A device in which biotin molecules were immobilized to the inner wall of a tube as a model probe, and a solution was introduced into the tube, which contained fluorescently tagged streptavidin as a model target molecule has been described (11). In that device, electromagnetic radiation was delivered from a source perpendicular to the tube, and that portion of the emitted fluorescence that happened to be coupled into the wall of the tube was detected by an optical system that captured light only from the tube wall.

In contrast, the core concept underlying the fluidic waveguide sensor of the present invention is the use of the fluid contained in a tube or container, either alone or in conjunction with other components of the system, as a waveguide or composite waveguide. The elements or components that can form composite fluidic waveguides include, in addition to the fluid contained in the chamber or tube, the probe layer, the tube wall, and coatings on the inner and outer surfaces of the tube or chamber. Various combinations and permutations of these elements can be employed to form composite fluidic waveguides. The advantage of this design is that it allows a substantially larger fraction of emitted light to be captured and guided to the detector, thereby resulting in greater efficiency and sensitivity.

Tubes have also been used in biosensors (1,12,13), wherein fluorescent reporter molecules are pre-bound to a probe molecule, which is in turn attached to the wall of the tube. When target molecules are transported through the system, they displace the fluorescent reporter molecules. These are flushed through the tube to a downstream fluorescence detector, where they are quantified. This system clearly differs from the fluidic waveguide sensor of the present invention in that it does not employ waveguide principles in the optics of the detection system and does not integrate the tube, or the fluid contained therein, optically into the sensor design, but uses the tube only as a reaction vessel for the chemical/biochemical components of the analytical process.

The invention described herein is not restricted as to the kinds of compounds, bio-molecules or biological entities that it can detect or quantify. However, all of these can be understood and described within the context of the probe-target-reporter model described in the following paragraphs.

Interactions between molecules can be highly specific. Such interactions can serve as the basis for a detection system. For instance, if Molecule A interacts with Molecule B in a highly specific manner, and if one has available a system for detecting that interaction, then it is often possible to design a system that uses Molecule A as a detector for Molecule B or visa versa.

Such systems consist of three basic elements:
1. The probe molecule. This is that component or participant in the molecular interaction that has been chosen to play a functional role in the analytical system.
2. The target molecule or analyte. This is the other participant in the molecular interaction, the participant that the analytical system is designed to detect or quantify.
3. The indicator or reporter molecule or system. This is a third molecule or chemical/physical system whose function, as part of the analytical system, is to indicate or "report" whether or not, and to what extent, target molecules may have interacted with probe molecules.

The following embodiments provide non-limiting representative examples of different probe-target-reporter systems that may be used in the assay and assay product of the present invention. In all cases, interaction of probe and target takes place within a fluidic waveguide or in another vessel and is subsequently introduced into a fluidic waveguide. The reporter system is designed to transduce the molecular interaction between probe and target molecules into an optical signal, which is then guided to the optical detector of the system. In addition, there are instances in which elements of one system described in these paragraphs can be used interchangeably in a second system. For instance, fluorescently labeled aptamers could be used as the indicator system for detection of the formation of probe-target complexes consisting of an antigen bound to an antibody.

In a preferred embodiment, nucleic acid molecules (or analogs thereof), including synthetic oligonucleotides, PCR amplicons, and cDNA molecules that correspond in sequence to the target nucleic acid molecules of interest, will function as the probe. Nucleic acid molecules complementary to the probe, which interact with it through mechanisms that rely primarily on hydrogen bonding, will function as the target or analyte.

Reporters useful with such probe-target pairs include:
A. An intercalating dye that binds specifically to double stranded DNA, which fluoresces to a much greater degree when bound to double stranded DNA than when free in solution, can function as the reporter in this system. Such a dye will serve as an indicator of the formation of complexes between probe and target nucleic acid molecules. Useful dyes are well known in the art and may include such entities as ethidium bromide.
B. Dyes can be incorporated directly into the target nucleic acid molecules, themselves, such that interaction of target with probe is accompanied by accumulation of dye molecules at the inner surface of the wall of the tubular sensor element.
C. A third nucleic acid molecule, which is labeled with a fluorescent dye, and can hybridize to a region of the target molecule that is in close proximity to the site where the probe nucleic acid molecule hybridizes, can be used to indirectly label probe-target complexes.

Another embodiment is an antibody that recognizes a molecule or class of molecules of interest. Here, a protein or other biological or synthetic molecule of interest serves as the analyte or target for the antibody probe.

Reporters useful with the such probe-target combinations include:
A. A second antibody that recognizes the target molecule and that is labeled directly with a fluorescent dye, such that it can be used as an indicator of the formation of complexes between probe and target.
B. A second antibody that recognizes the target molecule and that has been modified to carry out a second function in addition to recognition and binding of the target molecule. This second function serves to generate a fluorescent or colored product that can be measured by the analytical system, serving as an indicator of the formation of complexes between probe and target.

A third type of embodiment is an aptamer that recognizes a molecule or class of molecules that is of interest analytically. The targets can be proteins, nucleic acids, and other biomolecules and synthetic molecules that are recognized by, and can bind to, the aptamer. A second aptamer, the indicator aptamer, functions as the reporter in this system. The indicator aptamer binds to another region of the target molecule, or binds to the immobilized aptamer-target molecular complex. The indicator aptamer must be modified to carry a dye molecule or be linked to a catalytic element that can generate an indicator substance (fluorescent) while this aptamer is bound to the probe-target complex.

Another embodiment is an antigen used as a probe of sera to detect the presence of IgE antibodies specific for that antigen. Such a probe functions as an indicator that the serum donor is allergic to that antigen. An antibody, typically IgE, recognized by the probe antigen, functions as the target. The reporter is a second antibody specific for human IgE, which has been labeled with a fluorescent dye.

Other examples are receptors, such as hormone receptors, or other proteins, such as avidin, that bind with high specificity and high affinity to another biomolecule or synthetic molecule. Molecular species or complex recognized by the probe function as target, and examples of appropriate reporters are as follows:
A. A molecular species identical with or similar to the target molecule will be labeled with fluorescent dye. The probe molecules attached to the wall of the tubular sensor element will be saturated with this labeled molecular species. When an unknown that contains target molecules is introduced into the system the target molecules will displace the fluorescently labeled indicator molecules, which will be flushed from the sensor, reducing the fluorescent signal measured by the detector.
B. Alternatively, the fluorescence displaced from the walls of the tubular sensor element into the solution present in the lumen of the sensor tube could be measured directly using optics that can differentiate between fluorescence free in solution in the lumen of the tube and fluorescence immobilized to the walls of the tubular sensor element.

One additional type of embodiment is an enzyme specific for the target compound. An analyte of interest, which is recognized with high specificity by the probe, functions as target. The probe enzyme catalyzes the conversion of target analyte to a second compound. In some cases, this compound might, itself, be fluorescent and thus be directly detectable using the optics of the sensor system. Alternatively, the compound generated by the initial reaction could serve as a substrate for a second enzymatic reaction that would generate a fluorescent compound. The second enzyme could be either bound to the wall of the tubular sensor element or present in solution in the lumen of the container. Example: The enzyme luciferase could be attached to the container walls. This enzyme catalyzes an ATP- and luciferin-dependent reaction, generating light. Introducing into the sensor a sample of unknown composition that has been fortified with luciferin will lead to the generation of light if and only if ATP is present in the unknown. The extent of light production will be proportional to the amount of ATP present. Thus, this system can be used to quantify ATP levels in biological materials.

The fluidic waveguide technology addresses a critical need in the biosensor field, namely the need for sensitive and versatile analytical or detector elements or modules that can be readily integrated into fluidic systems. Other elements or modules are also very important, such as modules that combine and mix additional reagents with the sample, and modules that can fractionate complex mixtures of biological molecules or cells. However, an expanded range of detector systems for fluidic systems is a critical need. The fluidic waveguide constitutes a new and powerful class of analytical elements that fulfills this need.

In accordance with the foregoing, the present invention relates to a method of determining an analyte in a sample comprising contacting said analyte with a waveguide or lightguide of the invention, including manifolds of these, contacting said waveguide or lightguide with electromagnetic radiation and detecting a signal wherein said signal indicates the presence of said analyte in said sample, thereby determining said analyte in said sample.

When said waveguide comprises a optical coating, said optical coating element is thicker than one wavelength, preferably more than two wavelengths, of said electromagnetic radiation.

In preferred embodiments of the methods of the invention, the source of electromagnetic radiation is a laser or a white light source.

In additional preferred embodiments, the intensity of said signal is proportional to the amount of said analyte in said sample and/or wherein said detecting a signal comprises detecting electromagnetic radiation. In one preferred embodiment, the signal is produced by a fluorescent molecule.

In another preferred embodiment of the methods of the invention, the analyte comprises a reporter molecule that generates a signal when the probe is contacted with the analyte.

In another embodiment, probes, and/or targets (analytes), and/or reporters undergo biochemical, and/or chemical, and/or physical processes in another container, wherein said processes generate fluorescent complexes and/or derivatives from said probes, targets (analytes), and reporters, and said complexes and/or derivatives are transported to, and introduced into, a fluidic waveguide, in which detection of said fluorescent complexes and/or derivatives takes place.

For example, the waveguide or lightguide may comprise a reporter molecule, with or without a probe. Thus, the waveguide or lightguide is available for use in detection, either qualitative or quantitative, and without a probe, of the occurrence of a reaction, such as a chemical reaction, whereby the products are permitted to enter the fluid of the waveguide where the reporter is contacted with said products to provide a signal indicating the occurrence or extent of such reaction. The reporter molecule may react with one or more of said products and may include a fluorescent molecule or other label. The reporter may also comprise reagents that combine or otherwise react to form, for example, a fluorescent label that intern provides the appropriate detectable signal. The products of the reaction may themselves comprise a reporter molecule, such as a fluorescent label. All such embodiments, based on the devices and methods disclosed herein, are specifically contemplated by the present invention and other embodiments in keeping with the disclosure herein will no doubt suggest themselves to those of skill in the art.

REFERENCES

1. Rabbany, S. Y., Donner, B. L., and Ligler, F. S. (1994) *Crit Rev Biomed Eng* 22, 307–346
2. Gunasingham, H., and Tan, C. H. (1992) *Biosens Bioelectron* 7, 353–359
3. Schaffar, B. P., and Wolfbeis, O. S. (1990) *Biosens Bioelectron* 5, 137–148
4. Yeakley, J. M., Fan, J. B., Doucet, D., Luo, L., Wickham, E., Ye, Z., Chee, M. S., and Fu, X. D. (2002) *Nat Biotechnol* 20, 353–358.
5. Plowman, T. E., Durstchi, J. D., Wang, H. K., Christensen, D. A., Herron, J. N., and Reichert, W. M. (1999) *Anal Chem* 71, 4344–4352
6. Golden, J. P., Anderson, G. P., Rabbany, S. Y., and Ligler, F. S. (1994) *IEEE Trans Biomed Eng* 41, 585–591
7. Deacon, J. K., Thomson, A. M., Page, A. L., Stops, J. E., Roberts, P. R., Whiteley, S. C., Attridge, J. W., Love, C. A., Robinson, G. A., and Davidson, G. P. (1991) *Biosens Bioelectron* 6, 193–199
8. Piunno, P. A., Krull, U. J., Hudson, R. H., Damha, M. J., and Cohen, H. (1995) *Anal Chem* 67, 2635–2643
9. Pollard-Knight, D., Hawkins, E., Yeung, D., Pashby, D. P., Simpson, M., McDougall, A., Buckle, P., and Charles, S. A. (1990) *Ann Biol Clin* (Paris) 48, 642–646
10. Quinn, J. G., O'Neill, S., Doyle, A., McAtamney, C., Diamond, D., MacCraith, B. D., and O'Kennedy, R. (2000) *Anal Biochem* 281, 135–143
11. Misiakos, K., and Kakabakos, S. E. (1998) *Biosens Bioelectron* 13, 825–830
12. Wemhoff, G. A., Rabbany, S. Y., Kusterbeck, A. W., Ogert, R. A., Bredehorst, R., and Ligler, F. S. (1992) *J Immunol Methods* 156, 223–230
13. Kusterbeck, A. W., Wemhoff, G. A., Charles, P. T., Yeager, D. A., Bredehorst, R., Vogel, C. W., and Ligler, F. S. (1990) *J Immunol Methods* 135,191–197

What is claimed is:

1. A fluidic waveguide comrpising a container having walls forming a cavity each wall having an inner and an outer surface and a fluid that fills said cavity, wherein said fluid has a refractive index greater than the refractive index of the inner surface of said walls of said container forming said cavity and wherein said fluid acts as a waveguide when contacted with excitory electromacinetic radiation further comprising a probe or reporter in the cavity of the container wherein said probe or reporter is attached to the inner surface of a wall of the container.

2. The fluidic waveguide of claim 1 wherein said probe is a member selected from the group consisting of an oligonucleotide, an antibody, an aptamer, a catalyst and an enzyme and said reporter molecule is a member selected from the group consisting of a fluorophore and reagents that produce a fluorophore when said probe is contacted with an analyte.

3. The fluidic waveguide of claim 1 wherein said reporter molecule is attached to the inner surface of a wall of said container.

4. The fluidic waveguide of claim 1 wherein said reporter molecule is a quantum dot.

5. The fluidic waveguide of claim 1 wherein said probe is attached to the inner surface of a wall of said container.

6. The fluidic waveguide of claim 1 wherein said fluid is a liquid.

7. A fluidic waveguide of comprising a container having walls forming a cavity each wall having an inner and an outer surface and a fluid that fills said cavity, wherein said fluid has a refractive index less than or equal to the refractive index of the walls of said container, wherein the outer surface of the walls of said container is covered by an external medium, wherein the walls of said container have a refractive index greater than the refractive index of said external medium, and wherein said fluid and the walls of said container function together as a waveguide when contacted with excitory electromagnetic radiation wherein said probe is in solution in the fluid that fills said cavity.

8. The fluidic waveguide of claim 7 wherein said probe is a member selected from the group consisting of an oligonucleotide, an antibody, an aptamer, a catalyst and an enzyme.

9. The fluidic waveguide of claim 7 further comprising a reporter molecule.

10. The fluidic waveguide of claim 9 wherein said reporter molecule is a member selected from the group consisting of a fluorophore and reagents capable of producing a fluorophore.

11. The fluidic waveguide of claim 9 wherein said reporter is a quantum dot.

12. The fluidic waveguide of claim 7 wherein said fluid is a liquid.

13. A fluidic waveguide comprising a container having walls forming a cavity each wall having an inner and an outer surface and a fluid that fills said cavity, wherein:
(a) said fluid has a refractive index greater than the refractive index of the inner surface of said walls of said container forming said cavity and wherein said fluid acts as a waveguide when contacted with excitory electromagnetic radiation; or
(b) said fluid has a refractive index less than or equal to the refractive index of the walls of said container, wherein the outer surface of the walls of said container is covered by an external medium, wherein the walls of said container have a refractive index greater than the refractive index of said external medium, and wherein said fluid and the walls of said container function together as a waveguide when contacted with excitory electromagnetic radiation, further comprising a solid in said cavity wherein said probe is attached to said solid present in the cavity of the container.

14. The fluidic waveguide of claim 13 wherein said probe is a member selected from the group consisting of an oligonucleotide, an antibody, an aptamer, a catalyst and an enzyme.

15. The fluidic waveguide of claim 13 further comprising a reporter molecule.

16. The fluidic waveguide of claim 15 wherein said reporter molecule is a member selected from the group consisting of a fluorophore and reagents capable of producing a fluorophore.

17. The fluidic waveguide of claim 15 wherein said reporter is a quantum dot.

18. The fluidic waveguide of claim 13 wherein said fluid is a liquid.

19. A fluidic waveguide comprising a container having walls forming a cavity each wall having an inner and an outer surface and a fluid that fills said cavity, wherein said fluid has a refractive index greater than the refractive index of the inner surface of said walls of said container forming said cavity and wherein said fluid acts as a waveguide when contacted with excitory electromagnetic radiation wherein the inner surface of the walls of said container is covered by an optical coating and said fluid has a refractive index higher than the refractive index of said covered inner surface of the walls and further comprising a probe in the cavity of the container.

20. The fluidic waveguide of claim 19 wherein said coating has a thickness of at least 100 Angstroms.

21. The fluidic waveguide of claim 19 wherein said coating has a thickness of at least 100 Angstroms but not more than one micrometer.

22. The fluidic waveguide of claim 19 wherein said coating has a thickness of at least 500 Angstroms but not more than one micrometer.

23. The fluidic waveguide of claim 19 wherein said coating has a thickness of at least 0.1 micrometer but not more than one micrometer.

24. The fluidic waveguide of claim 19 wherein said coating has a thickness of at least one micrometer.

25. The fluidic waveguide of claim 19 wherein said probe is attached to the inner surface of a wall of the container.

26. The fluidic waveguide of claim 19 wherein said probe is in solution in the fluid that fills said cavity.

27. The fluidic waveguide of claim 19 further comprising a solid in said cavity wherein said probe is attached to said solid present in the cavity of the container.

28. The fluidic waveguide of claim 19 wherein said probe is a member selected from the group consisting of an oligonucleotide, an antibody, an aptamer, a catalyst and an enzyme.

29. The fluidic waveguide of claim 19 further comprising a reporter molecule.

30. The fluidic waveguide of claim 29 wherein said reporter molecule is a member selected from the group consisting of a fluorophore and reagents capable of producing a fluorophore.

31. The fluidic waveguide of claim 19 further comprising one or more reporter molecules that generate a signal when said probe is contacted with an analyte.

32. The fluidic waveguide of claim 31 wherein said probe is a member selected from the group consisting of an oligonucleotide, an antibody, an aptamer, a catalyst and an enzyme and said reporter molecule is a member selected from the group consisting of a fluorophore and reagents that produce a fluorophore when said probe is contacted with an analyte.

33. The fluidic waveguide of claim 31 wherein said reporter molecule is attached to the inner surface of a wall of said container.

34. The fluidic waveguide of claim 31 wherein said reporter molecule is a quantum dot.

35. A fluidic waveguide comprising a container and a fluid that fills said container, wherein said fluid has a refractive index less than or equal to the refractive index of the walls of said container, wherein the outer surface of the walls of said container is covered by an external medium, wherein the walls of said container have a refractive index greater than the refractive index of said external medium and wherein said fluid and the walls of said container function together as a waveguide when contacted with excitatory electromagnetic radiation and further comprising a probe wherein said probe is in solution in the fluid that fills said cavity.

36. The fluidic waveguide of claim 35 further comprising one or more reporter molecules that generate a signal when said probe is contacted with an analyte.

37. The fluidic waveguide of claim 36 wherein said probe is a member selected from the group consisting of an oligonucleotide, an antibody, an aptamer, a catalyst and an enzyme and said reporter molecule is a member selected from the group consisting of a fluorophore and reagents that produce a fluorophore when said probe is contacted with an analyte.

38. A fluidic waveguide comprising a container and a fluid that fills said container, wherein said fluid has a refractive index less than or equal to the refractive index of the walls of said container, wherein the outer surface of the walls of said container is covered by an external medium, wherein the walls of said container have a refractive index greater than the refractive index of said external medium and wherein said fluid and the walls of said container function together as a waveguide when contacted with excitatory electromagnetic radiation and further comprising a reporter molecule.

39. The fluidic waveguide of claim 38 wherein said reporter molecule is a member selected from the group consisting of a fluorophore and reagents capable of producing a fluorophore.

40. The fluidic waveguide of claim 38 wherein said reporter molecule is attached to the inner surface of a wall of said container.

41. The fluidic waveguide of claim 38 wherein said reporter molecule is a quantum dot.

42. The fluidic waveguide of claim 38 wherein said fluid is a liquid.

43. A fluidic waveguide comprising a container having walls forming a cavity each wall having an inner and an outer surface and a fluid that fills said cavity, wherein:
  (a) said fluid has a refractive index greater than the refractive index of the inner surface of said walls of said container forming said cavity and wherein said fluid acts as a waveguide when contacted with excitory electromagnetic radiation; or
  (b) said fluid has a refractive index less than or equal to the refractive index of the walls of said container, wherein the outer surface of the walls of said container is covered by an external medium, wherein the walls of said container have a refractive index greater than the refractive index of said external medium, and wherein said fluid and the walls of said container function together as a waveguide when contacted with excitory electromagnetic radiation wherein said fluid is a gel.

44. The fluidic waveguide of claim 43 further comprising a probe in the cavity.

45. The fluidic waveguide of claim 44 wherein said probe is a member selected from the group consisting of an oligonucleotide, an antibody, an aptamer, a catalyst and an enzyme.

46. The fluidic waveguide of claim 44 further comprising one or more reporter molecules that generate a signal when said probe is contacted with an analyte.

47. The fluidic waveguide of claim 46 wherein said one or more reporter molecules are members selected from the group consisting of a fluorophore and reagents capable of producing a fluorophore.

48. The fluidic waveguide of claim 43 further comprising a reporter in the cavity.

49. The fluidic waveguide of claim 48 wherein said reporter molecule is a member selected from the group consisting of a fluorophore and reagents capable of producing a fluorophore.

50. A fluidic waveguide comprising a container having walls forming a cavity each wall having an inner and an outer surface and a fluid that fills said cavity, wherein said fluid has a refractive index greater than the refractive index of the inner surface of said walls of said container forming said cavity and wherein said fluid acts as a waveguide when contacted with excitory electromagnetic radiation wherein the outer surface of the walls of the container are coated with a reflective material such that electromagnetic radiation is reflected back into the waveguide.

51. The fluidic waveguide of claim 50 further comprising a probe in the cavity.

52. The fluidic waveguide of claim 50 further comprising one or more reporter molecules in the cavity.

* * * * *